US012746260B2

(12) United States Patent
Labiad-Hadji et al.

(10) Patent No.: US 12,746,260 B2
(45) Date of Patent: Sep. 29, 2026

(54) **EXTRACT OF BACTERIA OF THE GENUS *Sphingomonas***

(71) Applicant: L'OREAL, Paris (FR)

(72) Inventors: Karima Labiad-Hadji, Aulnay-sous-Bois (FR); Cosima Dufour-Schroif, Aulnay-sous-Bois (FR); Gayané Azadiguian, Aulnay-sous-Bois (FR); Sylvie Bun, Aulnay-sous-Bois (FR)

(73) Assignee: L'OREAL, Paris (FR)

( * ) Notice: Subject to any disclaimer, the term of this patent is extended or adjusted under 35 U.S.C. 154(b) by 381 days.

(21) Appl. No.: 18/257,113

(22) PCT Filed: Dec. 17, 2021

(86) PCT No.: PCT/EP2021/086534
§ 371 (c)(1),
(2) Date: Jun. 13, 2023

(87) PCT Pub. No.: WO2022/129549
PCT Pub. Date: Jun. 23, 2022

(65) Prior Publication Data

US 2024/0024379 A1 Jan. 25, 2024

(30) Foreign Application Priority Data

Dec. 18, 2020 (FR) ........................................ 2013724
Aug. 31, 2021 (FR) ........................................ 2109095

(51) Int. Cl.
*A61K 35/74* (2015.01)
*A61K 9/00* (2006.01)
*A61K 33/00* (2006.01)
*A61K 36/537* (2006.01)
*A61K 38/05* (2006.01)
*A61P 37/08* (2006.01)

(52) U.S. Cl.
CPC ............ *A61K 35/74* (2013.01); *A61K 9/0014* (2013.01); *A61K 33/00* (2013.01); *A61K 36/537* (2013.01); *A61K 38/05* (2013.01); *A61P 37/08* (2018.01)

(58) Field of Classification Search
None
See application file for complete search history.

(56) References Cited

U.S. PATENT DOCUMENTS

| | | | |
|---|---|---|---|
| 9,295,722 | B2 | 3/2016 | Savage et al. |
| 2002/0006414 | A1 | 1/2002 | Murata et al. |
| 2009/0028805 | A1 | 1/2009 | Gueniche et al. |
| 2014/0044653 | A1 | 2/2014 | Qvit-Raz et al. |
| 2014/0044677 | A1 * | 2/2014 | Qvit-Raz ............. A61K 35/744 435/252.32 |
| 2019/0343898 | A1 | 11/2019 | Sinkkonen et al. |

FOREIGN PATENT DOCUMENTS

| | | | |
|---|---|---|---|
| CN | 109234180 | A | 1/2019 |
| EP | 0887070 | A1 | 12/1998 |
| EP | 1716857 | A1 | 11/2006 |
| EP | 3896174 | A1 | 10/2021 |
| FR | 2700470 | A1 | 7/1994 |
| JP | H10330273 | A | 12/1998 |
| JP | 2003250547 | A | 9/2003 |
| JP | 2005263797 | A | 9/2005 |
| JP | 2008528608 | A | 7/2008 |
| JP | 2010208949 | A | 9/2010 |
| JP | 2017214323 | A | 12/2017 |
| KR | 20200070991 | A | 6/2020 |
| NL | 2020080 | * | 6/2018 |
| WO | 2006083671 | A2 | 8/2006 |
| WO | 2006083671 | A3 | 8/2006 |
| WO | 2020122450 | A1 | 6/2020 |

OTHER PUBLICATIONS

International Search Report and Written Opinion issued on Mar. 16, 2022 for corresponding PCT Application No. PCT/EP2021/086534.
Gou, Min et al.: "Characterization of catechol 1,2-dioxygenase from cell extracts of Sphingomonas xenophaga QYY", Science in China. Series B: Chemistry, vol. 52, No. 5, May 2009, pp. 615-620 XP055835017.
Jiao, L. et al.: "Quinone-mediated decolorization of sulfonated azo dyes by cells and cell extracts from Sphingomonas xenophaga", Journal of Environmental Sciences, Elsevier BV, NL, vol. 21, No. 4, 2009, pp. 503-508 XP026044462.
Yuanyuan Qu et al.: "Bioaugmentation of Bromoamine Acid Degradation with Sphingomonas xenophaga QYY and DNA Fingerprint Analysis of Augmented Systems", Biodegradation, Kluwer Academic Publishers, DO, vol. 17, No. 1, 2006, pp. 83-91 XP019231953.
David Schleheck et al.; "Saccharin as a sole source of carbon and energy for Sphingamooas xenophaga SKN," Arch. Microbiol., vol. 179, 2003, pp. 191-196.

* cited by examiner

*Primary Examiner* — Brian Gangle
(74) *Attorney, Agent, or Firm* — POLSINELLI PC

(57) ABSTRACT

The present invention relates to an extract of bacteria of the genus *Sphingomonas*, and compositions comprising an extract of bacteria of the genus *Sphingomonas* or at least one bacterium of the genus *Sphingomonas* for use in the prevention and/or the treatment of cutaneous reactions caused by an allergic reaction and for use in the modulation of the immune response and optionally in the reinforcement of the barrier function of the skin.

17 Claims, 1 Drawing Sheet

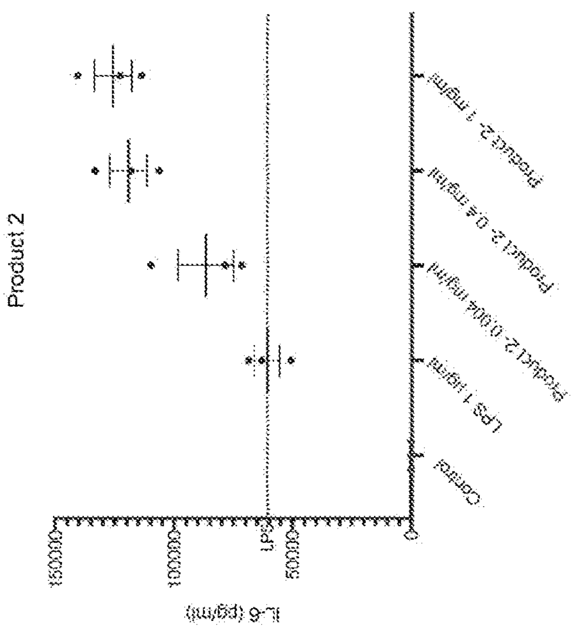
Product 2
IL-6 (pg/ml)
150000
100000
50000
LPS
0
Control
LPS 1 ug/ml
Product 2- 0.004 mg/ml
Product 2- 0.4 mg/ml
Product 2- 1 mg/ml
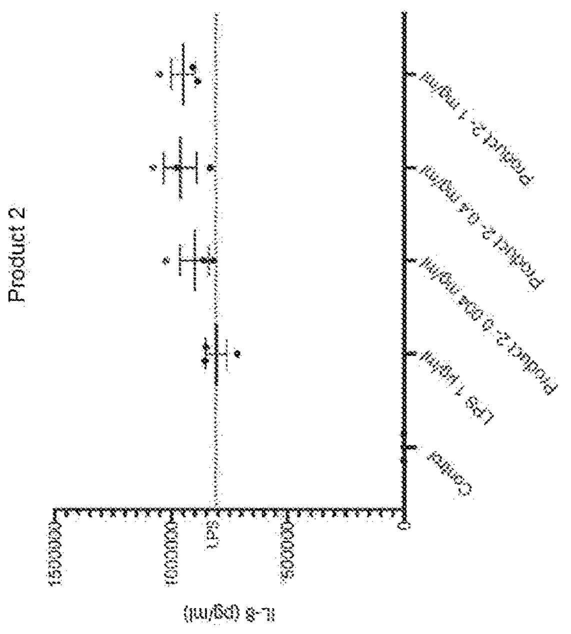
Product 2
IL-8 (pg/ml)
1500000
1000000
500000
LPS
0
Control
LPS 1 ug/ml
Product 2- 0.004 mg/ml
Product 2- 0.4 mg/ml
Product 2- 1 mg/ml
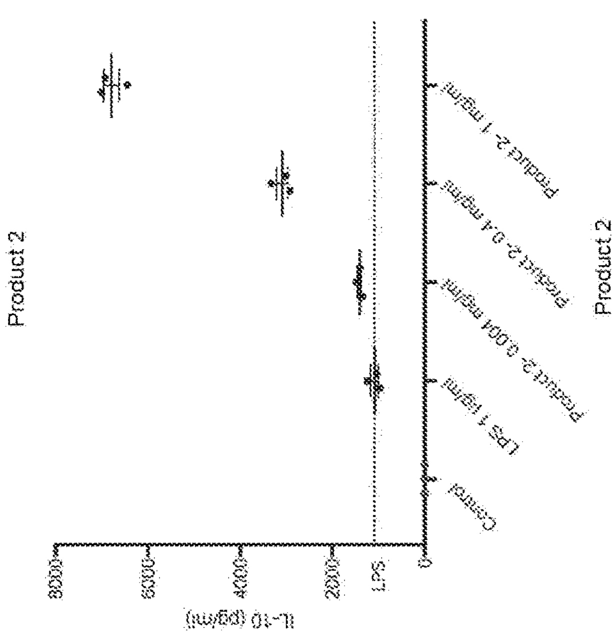
Product 2
IL-10 (pg/ml)
8000
6000
4000
2000
LPS
0
Control
LPS 1 ug/ml
Product 2- 0.004 mg/ml
Product 2- 0.4 mg/ml
Product 2- 1 mg/ml
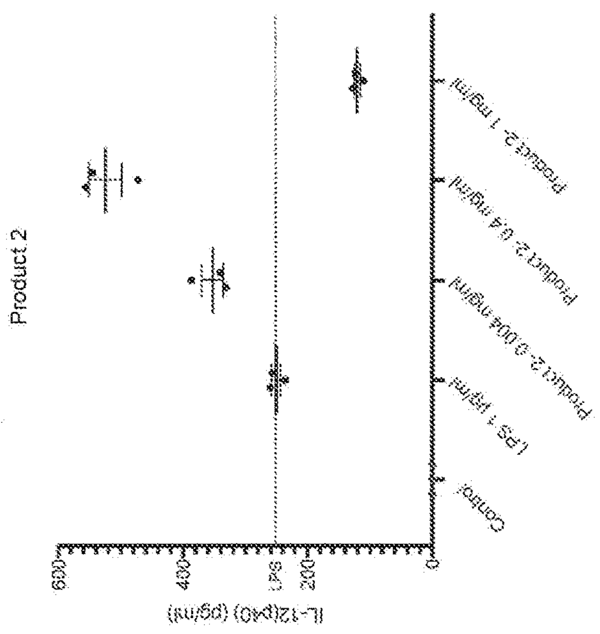
Product 2
IL-12(p40) (pg/ml)
600
400
200
LPS
0
Control
LPS 1 ug/ml
Product 2- 0.004 mg/ml
Product 2- 0.4 mg/ml
Product 2- 1 mg/ml

EXTRACT OF BACTERIA OF THE GENUS *Sphingomonas*

CROSS-REFERENCE TO RELATED APPLICATIONS

This application is a national stage application (under 35 U.S.C. § 371) of PCT/EP2021/086534, filed Dec. 17, 2021, which claims benefit of French Application No. 2013724, filed Dec. 18, 2020, and French Application No. 2109095, filed Aug. 31, 2021, disclosures of which are incorporated herein by reference in their entirety.

The present invention relates to an extract of bacteria of the genus *Sphingomonas*, and compositions comprising an extract of bacteria of the genus *Sphingomonas* or at least one bacterium of the genus *Sphingomonas* for use in the prevention and/or the treatment of cutaneous reactions caused by an allergic reaction and for use in the modulation of the immune response and optionally in the reinforcement of the barrier function of the skin.

The allergy is a complex phenomenon wherein an exaggerated inflammatory reaction occurs following the exposure of the organism to an allergen. In particular, the allergy depends on two valences, the porosity of the barrier between the organism and the external medium and the regulation of the immune system.

Thus, the allergy depends on the permeability of the skin which is a barrier against external, in particular particle, chemical or chemical, aggressions but also in order to limit the leakage of water and other interstitial compounds. This property of the skin is called barrier function. In particular, the barrier function is ensured by the tight junctions and the associated proteins. By stimulating the expression of these proteins and the formation of the tight junctions, the activation of the Toll 2 (TLR2) type receptors allows reinforcing the barrier function.

The allergy also depends on the regulation of the immune system, in particular via type E antibodies (IgE), prostaglandin E2 ($PGE_2$) and various interleukins (IL).

The IgE participate in the immediate-type allergic reaction which could cause an urticaria or an angioedema.

$PGE_2$ and IL-6/IL-8 also have a role in the attraction of neutrophils. They have a complementary mode of action, on the one hand, thanks to an increase of the vascular permeability for $PGE_2$ and, on the other hand, through a gradient of chemokines attracting neutrophils for IL-6 or IL-8. Hence, these two different and combined modes of action improve the immune response.

The inventors have discovered that an extract of *Sphingomonas* allows activating the hTLR2 receptors in vitro, and promoting the expressions of genes related to the reinforcement of the barrier function of the skin. They have also shown that this extract allows inhibiting the secretion of the pro-inflammatory mediator $PGE_2$ and modulating the expressions of interleukins promoting IL-10 (anti-inflammatory cytokine) without significantly affecting the other pro-inflammatory interleukins such as IL-12, IL-6 and IL-8. Finally, the inventors have shown that the extract allowed limiting the IgE production by human B lymphocytes.

Thus, the bacteria of the genus *Sphingomonas* and their extracts have several anti-inflammatory activities combined with a reinforcement of the barrier function of the skin enabling the prevention and/or the treatment of cutaneous reactions caused by an allergic reaction.

Thus, the present invention relates to an extract of bacteria of the genus *Sphingomonas* for use in the prevention and/or the treatment of cutaneous reactions caused by an allergic reaction.

The present invention also relates to a composition comprising an extract of bacteria of the genus *Sphingomonas* or at least one bacterium of the genus *Sphingomonas* for use in the prevention and/or the treatment of cutaneous reactions caused by an allergic reaction.

The present invention also relates to an extract of bacteria of the genus *Sphingomonas* for use in the modulation of the immune response and optionally in the reinforcement of the barrier function of the skin.

Furthermore, the present invention relates to a composition comprising an extract of bacteria of the genus *Sphingomonas* or at least one bacterium of the genus *Sphingomonas*, for use in the modulation of the immune response and optionally in the reinforcement of the barrier function of the skin.

DETAILED DESCRIPTION OF THE INVENTION

General Definitions

The term "bacterium" refers to a procaryotic microorganism, preferably a proteobacterium, in a living, semi-active, inactivated or dead form.

The used bacterium according to the invention or the bacterium of the used extract according to the invention is of the genus *Sphingomonas*. In one embodiment, the bacterium is of a species selected amongst *Sphingomonas abaci, Sphingomonas adhaesiva, Sphingomonas aerolata, Sphingomonas aquatilis, Sphingomonas asaccharolytica, Sphingomonas aurantiaca, Sphingomonas azotifigens, Sphingomonas dokdonensis, Sphingomonas echinoides, Sphingomonas faeni, Sphingomonas fennica, Sphingomonas haloaromaticamans, Sphingomonas jaspsi, Sphingomonas koreensis, Sphingomonas mall, Sphingomonas melonis, Sphingomonas natatoria, Sphingomonas oligophenolica, Sphingomonas panni, Sphingomonas parapaucimobilis, Sphingomonas paucimobilis, Sphingomonas phyllosphaerae, Sphingomonas pituitosa, Sphingomonas pruni, Sphingomonas roseiflava, Sphingomonas sanguinis, Sphingomonas soli, Sphingomonas* sp, *Sphingomonas suberifaciens, Sphingomonas trueperi, Sphingomonas wittichii, Sphingomonas xenophaga, Sphingomonas yabuuchiae, Sphingomonas yunnanensis*, and *Sphingomonas yanoikuyae*. In one embodiment of the invention, the bacterium is *Sphingomonas xenophaga*. In a preferred embodiment, the bacterium is a *Sphingomonas xenophaga* filed in compliance with Budapest Treaty, on Nov. 21, 2019, before the National Collection of microorganism culture ((CNCM), Paris, France) under the number CNCM I-5455 by L'Oreal, 101 Avenue Gustave Eiffel, 37390 Notre Dame d'Oe.

As used herein, the term "prevent" or "prevention" refers to any action that aims to prevent the apparition of a disorder or of one or several symptom(s) related to this disorder. Hence, this term also covers the slowdown, the discontinuation or the limitation of the symptoms.

As used herein, the term "treat" or "treatment" refers to any action that aims to suppress, alleviate or prevent the progress of a disorder of one or several symptom(s) related to this disorder. Hence, this term covers the attenuation, the relief or the suppression of the symptoms.

By "the prevention and/or the treatment of cutaneous reactions caused by an allergic reaction", it should be understood the slowdown, the discontinuation, the limitation, the attenuation, the relief or the suppression of the cutaneous symptoms caused by an allergic reaction in a subject. In general, these symptoms include urticaria, a cutaneous eruption and/or the apparition of redness.

By "subject", it should be understood herein a human being, preferably a human being suffering from an allergy. In an embodiment of the invention, the subject has already had allergic reactions having caused cutaneous reactions.

By "cutaneous", it should be understood at the level of the skin and more particularly at the level of the area of the skin exposed or likely to be exposed to an allergen. According to an embodiment of the invention, the cutaneous reactions caused by an allergic reaction include urticaria, a cutaneous eruption and/or the apparition of redness.

In a preferred embodiment, the extracts and compositions used in the context of the invention are used topically. In a preferred embodiment, the extracts and compositions used in the context of the invention are intended for an application on the skin.

In the context of the invention, the term "skin" refers to any cutaneous surface of the body, preferably the skin of the face, the skin of the neck, of the cleavage, and more particularly the skin of the face.

By "allergic reaction", it should be understood the meaning commonly used by a person skilled in the art i.e. an exaggerated inflammatory reaction that occurs following the exposure of the organism to an allergen. This reaction is the sign of a hypersensitivity of the organism to substances, generally inoffensive and present in the environment. allergens. These substances may be found in air, cosmetics, etc. . . . .

A so-called immediate allergic reaction is characterized by an apparition of the symptoms most often in few minutes (less than two hours) after contact with the allergen. In this case, this consists of an urticaria, which could spread and involve IgE. A so-called delayed allergic reaction is characterized by an apparition of the symptoms generally 48 hours after contact with the allergen. In this case, it consists of a local eczema at the contact site, involving chemical molecules.

In a preferred embodiment, the extracts and compositions implemented in the context of the invention are used in the prevention and/or the treatment of cutaneous reactions caused by an immediate-type allergic reaction.

By "the modulation of the immune response", it should be understood herein the slowdown, the discontinuation or the attenuation of the immune response. In particular, the modulation of the immune response according to the invention is a decrease in the activity of pro-inflammatory cytokines and/or an increase in the activity of anti-inflammatory cytokines.

In a preferred embodiment of the invention, the modulation of the immune response is achieved through the increase of the activity of IL-10 without significantly affecting the pro-inflammatory interleukins IL-12, IL-6 and/or IL-8.

By "reinforcement of the barrier function of the skin", it should be understood herein improving the barrier function of the skin, and in particular through the increase of the number of tight junctions and/or through the increase of the associated proteins such as Claudin-1, Cornifelin and/or Zonula Occludens 1 at the level of the skin.

Extract of Bacteria of the Genus *Sphingomonas*

The present invention relates to an extract of bacteria of the genus *Sphingomonas* for use in the prevention and/or the treatment of cutaneous reactions caused by an allergic reaction.

In the context of the invention, the term "extract of bacteria" refers to both a set of compounds produced and/or secreted by a bacterium, and therefore present in the culture medium of the bacterial culture (also called extracellular medium), and/or a set of compounds comprised in the bacterium, and therefore present in the bacterial pellet of the bacterial culture after centrifugation, like the intracellular medium and/or the constituents of the cellular walls and/or membranes.

The extracts according to the invention can be prepared by any conventional method well known to a person skilled in the art. Typically, these methods comprise a fermentation, separation and purification step.

Typically, the bacterium of the genus *Sphingomonas* is cultured in a suitable medium and cultured at a desired density. Preferably, the bacteria themselves are concentrated by any known process, such as centrifugation. Afterwards, the concentrated bacteria could be used directly as a raw preparation, or additional treatment steps well known to a person skilled in the art could be performed such as, lyophilization, dehydration, filtering, purification, freezing possibly followed by unfreezing, sterilization, column chromatography, crushing, lysis, etc.

Preferably, the bacterial extract is a bacterial lysate. Such a lysate comprising in particular the compounds comprised in the bacterium, and therefore present in the bacterial pellet of the bacterial culture after centrifugation. Preferably, the bacterial extract is a bacterial lysate comprising the intracellular medium and/or the constituents of the cellular walls and/or membranes.

A lysate commonly denotes a material obtained upon completion of the destruction or dissolution of biological cells by a phenomenon referred to as cell lysis thus inducing the release of the intracellular biological constituents naturally contained in the cells of the considered microorganism.

In the context of the present invention, the term lysate is indifferently used to refer to the entirety of the lysate obtained by lysis of the considered microorganism or only a fraction thereof.

Hence, the implemented lysate is totally or partially formed by the intracellular biological constituents and by the constituents of the cellular walls and membranes.

Hence, preferably, the implemented lysate is totally or partially formed essentially by the intracellular biological constituents and by the constituents of the cellular walls and membranes.

In a preferred embodiment, the lysate comprises less than 1% by dry weight of extracellular medium, still better the lysate comprises between 0.5% and 1% by dry weight of extracellular medium, still more preferably the lysate comprises between 0.7% and 0.8% by dry weight of extracellular medium.

This cellular lysis can be completed by different technologies, such as osmotic shock, thermal shock like freezing followed by unfreezing, by ultrasounds, by a high-pressure treatment or under a centrifugation-type mechanical stress for example.

Preferably, the lysate implemented in the context of the present invention is obtained by a method comprising the following steps:

i) a centrifugation step;

ii) a step of recovering the pellet;

iii) a step of freezing the pellet;
iv) a step of unfreezing the pellet;
v) optionally a step of sterilization by autoclaving, in particular at 121° C.

In a particular embodiment of the invention, the bacterial extract comprises an inactivated bacterium.

By "inactivated", it should be understood the meaning commonly used by a person skilled in the art i.e. The suppression of the activity of the bacterium under the effect of various causes (heat, chemical substances, mechanical, enzymatic). In particular, the bacterium is inactivated by heat, more particularly by autoclaving.

Preferably, said extract according to the invention has an activity in activating the hTLR2 receptors and/or in promoting the expression of genes related to the reinforcement of the barrier function of the skin.

Preferably, said extract has an activity in inhibiting the secretion of the pro-inflammatory mediator $PGE_2$.

Preferably, said extract has an activity in stimulating the expression of IL-10, without significantly impacting the expression of IL-12, IL-6 and IL-8.

Preferably, said extract has an activity in inhibiting the production of IgE by B lymphocytes.

All these activities can be detected and/or analyzed by techniques known to a person skilled in the art including particular examples described in the examples hereinafter.

Thus, the bacteria of the genus *Sphingomonas* and their extracts have several anti-inflammatory activities combined with a reinforcement of the barrier function of the skin enabling the prevention and/or the treatment of cutaneous reactions caused by an allergic reaction.

The present invention also relates to an extract of bacteria according to the invention for use in the modulation of the immune response and optionally in the reinforcement of the barrier function of the skin.

Composition

The present invention also relates to a composition, in particular intended for a topical application, comprising an extract of bacteria of the genus *Sphingomonas*, or at least one bacterium of the genus *Sphingomonas*, for use in the prevention and/or the treatment of cutaneous reactions caused by an allergic reaction.

The present invention also relates to a composition, comprising an extract of bacteria of the genus *Sphingomonas*, or at least one bacterium of the genus *Sphingomonas* for use in the modulation of the immune response and optionally in the reinforcement of the barrier function of the skin.

In one embodiment, the composition comprises an extract as described hereinabove.

In one embodiment, the composition comprises at least one bacterium of the genus *Sphingomonas* as described in the general definitions section.

The amount of bacteria or of extract of bacteria in the composition according to the invention varies depending on the considered composition type. Preferably, the amount of microorganisms or of extract is comprised between 0.0001 and 30% by dry weight with respect to the total weight of the composition, between 0.001 and 15% by dry weight with respect to the total weight of the composition, between 0.01 and 10% by dry weight with respect to the total weight of the composition, preferably between 0.01 and 5% by dry weight with respect to the total weight of the composition, or between 0.01 and 3% by dry weight with respect to the total weight of the composition.

In the case where the bacteria are formulated in a composition in a living form, the amount of live bacteria may vary from $10^3$ to $10^{15}$ ufc/g, in particular from $10^5$ to $10^{15}$ ufc/g and more particularly from $10^7$ to $10^{12}$ ufc/g of bacteria per gram of composition.

Preferably, the composition according to the invention comprises an aqueous phase.

Preferably, the composition according to the invention has a water content ranging from 20% to 95% by weight, and preferably from 30% to 70% by weight with respect to the total weight of the composition.

The composition according to the invention may further comprise one or several water-miscible organic solvent(s) at a concentration ranging from 0.5% to 25% by weight, preferably, from 5% to 20% by weight, and better from 10% to 15% by weight relative to the total weight of the composition.

As indicated before, the compositions used in the context of the invention are preferably used topically.

As this is well known to a person skilled in the art, compositions for topical application may also contain common additives, such as hydrophilic or lipophilic gelling agents, hydrophilic or lipophilic active substances different from the extract according to the invention, preservatives, antioxidants, solvents that are not miscible in water, perfumes, odor-absorbing agents, colorants. The amounts of these different additives are those commonly used in the considered field, for example from 0.01 to 20% of the total weight of the composition.

Of course, a person skilled in the art will take care of selecting these optional additional ingredients and/or active substances, and/or the amount thereof, such as the advantageous properties of the extract according to the invention are not, or are substantially not, altered by the considered addition.

In one embodiment, the bacteria of the genus *Sphingomonas* or the extract of bacteria of the genus *Sphingomonas* is the unique active substance of the composition.

In another embodiment, the composition of the invention may further contain other active substances different from the bacteria or the extract according to the invention. These active substances may have an effect on the skin and in particular a soothing effect.

In a particular embodiment of the invention, the composition according to the invention further comprises at least one active substance selected amongst acetyl dipeptide-1 cetyl ester, an extract of *Salvia* miltiorrhiza root, a thermal water such as La Roche Posay water, and mixtures thereof.

The compositions according to the invention may be in any galenic forms commonly used for a topical application and in particular in the form of aqueous, aqueous-alcoholic solutions, of oil-in-water (O/W) or water-in-oil (W/O) or multiple (triple: W/O/W or O/W/O) emulsions, of aqueous gels, or of dispersions of a fatty phase in an aqueous phase using spherules, these spherules may consist of ionic- and/or nonionic-type lipid vesicles (liposomes, niosomes, oleosomes). These compositions are prepared using routine methods.

Advantageously, the compositions according to the invention are in the form of gel, or emulsion, or paste. Furthermore, the composition according to the invention can be more or less fluid and have the appearance of a white or colored cream, of an ointment, of a milk, of a lotion, of a serum, of a paste, of a foaming or non-foaming gel, of an exfoliation, of a mask, of a treatment, of a tonic or of a foam. It could possibly be applied on the skin in the form of a spray. It could also be in a solid form, and for example be in the form of a stick or a soap.

A composition according to the invention may comprise a fatty phase, in particular an oily phase.

By way of oils suitable for use in the composition according to the invention, mention may be made for example of:

- hydrocarbon oils,
- synthetic esters and ethers, in particular of fatty acids, like the oils of formulas R'COOR2 and R'COR2 wherein R' represents the residue of a fatty acid including 8 to 29 carbon atoms, and R2 represents a hydrocarbon chain, branched or not, containing 3 to 30 carbon atoms;
- linear or branched hydrocarbons, from a mineral or synthetic origin;
- fatty alcohols having from 8 to 26 carbon atoms;
- partially hydrocarbonated and/or siliconized fluorinated oils;
- silicone oils;
- mixtures thereof.

By hydrocarbon oil in the list of oils cited above, it should be understood any oil including mostly carbon and hydrogen atoms.

The oily phase may include other fatty bodies that could be present in the oily phase, for example fatty acids including 8 to 30 carbon atoms; waxes, silicone resins; and silicone elastomers. These fats may be selected in varied ways by those skilled in the art in order to prepare a composition having the sought properties, for example consistency or texture properties.

According to a particular embodiment of the invention, the composition according to the invention is a water-in-oil (W/O) or oil-in-water (O/W) emulsion. The proportion of the oily phase of the emulsion may range from 5 to 80% by weight, and preferably from 30 to 70% by weight relative to the total weight of the composition. The emulsions generally contain at least one emulsifier selected from amphoteric, anionic, cationic or non-ionic emulsifiers, used alone or in a mixture, and optionally a co-emulsifier. The emulsifiers are suitably selected according to the emulsion to be obtained (W/O or O/W). In general, the emulsifier and the co-emulsifier are present, in the composition, in a proportion ranging from 0.3% to 30% by weight, and preferably from 0.5% to 20% by weight relative to the total weight of the composition.

For W/O emulsions, as emulsifiers, mention may be made for example of dimethicone copolyols and alkyl-dimethicone copolyols. It is also possible to use, as a surfactant of W/O emulsions, a cross-linked elastomer solid organopolysiloxane including at least one oxyalkylenated group.

For O/W emulsions, as emulsifiers, mention may be made for example of nonionic emulsifiers.

The composition may be rinsed or not after having been applied on the skin.

Methods

The present invention also relates to a method for preventing or treating cutaneous reactions caused by an allergic reaction comprising the administration, preferably topically at the surface of the skin, of an extract of bacteria of the genus *Sphingomonas* or of a composition comprising an extract of bacteria of the genus *Sphingomonas* or at least one bacterium of the genus *Sphingomonas*.

The use of an extract of bacteria of the genus *Sphingomonas* or of a composition comprising an extract of bacteria of the genus *Sphingomonas* or at least one bacterium of the genus *Sphingomonas* in the production of a medicine for the prevention or the treatment of cutaneous reaction caused by an allergic reaction is also proposed.

The present invention also relates to a method for modulating the immune reaction and optionally for reinforcing the barrier function of the skin, comprising the administration, preferably topically at the surface of the skin, of an extract of bacteria of the genus *Sphingomonas* or of a composition comprising an extract of bacteria of the genus *Sphingomonas* or at least one bacterium of the genus *Sphingomonas*.

The use of an extract of bacteria of the genus *Sphingomonas* or of a composition comprising an extract of bacteria of the genus *Sphingomonas* or at least one bacterium of the genus *Sphingomonas* in the production of a medicine for the modulation of the immune reaction and optionally the reinforcement of the barrier function of the skin, is also proposed.

In a particular embodiment, the composition comprising an extract of bacteria of the genus *Sphingomonas* or at least one bacterium of the genus *Sphingomonas* is as described in the composition section hereinabove.

In a particular embodiment, the extract of bacteria of the genus *Sphingomonas* is as described in the section extract of bacteria of the genus *Sphingomonas* hereinbelow.

Preferably, the application is performed on a subject who needs it and in an effective amount of at least one extract of bacteria of the genus *Sphingomonas* or of at least one composition comprising an extract of bacteria of the genus *Sphingomonas* or at least one bacterium of the genus *Sphingomonas*.

As used herein, the term "effective amount" refers to the amount of extract of bacteria of the genus *Sphingomonas* which, as a whole, allows preventing and/or reducing the cutaneous reactions caused by an allergic reaction, or to the amount of bacteria of the genus *Sphingomonas*, which, as a whole, allows preventing and/or reducing the cutaneous reactions caused by an allergic reaction.

The effective amount naturally depends on the considered active substance, on the administration mode, on the therapeutic indication, on the age of the patient and on his/her condition.

Advantageously, the composition or the extract is used in particular in the form of a dermatological composition, possibly further comprising a physiologically-acceptable excipient.

By "physiologically-acceptable", it should be understood herein compositions and molecular entities that do not generate undesired secondary reactions, allergic, or others, when they are administrated to a subject. Thus, a physiologically-acceptable excipient or vehicle is an encapsulating material, a diluent, a support, or any other liquid, semi-solid or solid non-toxic formulation auxiliary.

The dermatological compositions used in the context of the invention are typically prepared so as to adapt to the administration mode. The physiologically-acceptable excipients are typically determined partly by the administrated composition, as well as by the particular technique used to administer the composition.

The dosage of the compounds to be administered depends on the individual case and, as it is well known to a person skilled in the art, should be suited to the individual circumstances in order to obtain an effective amount and an optimum effect. The effective dose level is specific to every subject, and will depend in particular on various factors, including the disorder that is treated and the seriousness of the disorder, the activity of the specific compound that is used; the specific composition that is used. For example, it is well known to a person skilled in the art to start with doses of the compound at levels below those required to reach the desired effect and to progressively increase the dose until the desired effect is obtained.

Preferably, the methods according to the invention comprise the topical application of at least one bacterium of the genus *Sphingomonas* or of at least one extract of the genus *Sphingomonas* or of a composition comprising the same.

In a preferred embodiment, the topical application in the context of the invention is an application on the skin.

The methods of the invention may comprise one single administration. In another embodiment, the administration is repeated for example 2 to 3 times a day for one day or more, or a daily application for several consecutive days or not, and generally for an extended duration of at least 4 weeks or 4 to 15 weeks, or as long as necessary with a possible break where needed.

In another embodiment, the methods of the invention may comprise an administration on an area of the skin before and/or after an exposure of this area to an allergen.

In the description and in the following examples, unless stated otherwise, the percentages are percentages by weight and the value ranges worded as "between . . . and . . . " include the specified upper and lower limits. The ingredients are mixed, prior to the packaging thereof, in order and under conditions readily determined by a person skilled in the art.

The present invention will be illustrated further by the examples hereinbelow.

FIGURE

FIG. 1 represents the effect of the extract of *Sphingomonas* on the secretion of cytokines by the monocytes.

EXAMPLES

Example 1: Preparation of an Extract According to the Invention

A culture of the strain *Sphingomonas xenophaga* CNCM-I 5455, is made in a complete culture medium in a bioreactor of 3000 effective liters in batch mode. During this step, the pH is not regulated, the temperature is maintained at 26° C. and oxygen dissolved at 30%.

The composition of the initial culture medium is described in Table 1 hereinbelow.

TABLE 1

| Chemical name | concentration |
|---|---|
| Yeast autolytic extract | 4 g/l |
| F soy papainic peptone | 3 g/l |
| Glucose | 3 g/l |
| $KH_2PO_4$ | 0.088 g/l |
| $CaCl_2$ | 0.050 g/l |
| $CuSO_4$, 5 $H_2O$ | 60 g/l |
| $MnSO_4$, $1H_2O$ | 152 μg/l |
| KI | 20 μg/l |
| $ZnSO_4$, $7H_2O$ | 200 g/l |
| $AlCl_3$, $6H_2O$ | 100 μg/l |
| osmotic water | Q.S. 1 l |

Once the plateau level is reached, the extraction and the separation of the cells are carried out by centrifugation (10,000 g continuously). Then, the pellet, also called biomass, containing the cells is recovered, in order to be frozen at −20° C. afterwards and then unfrozen thereby enabling the explosion of the cells and thus the obtainment of a lysate. Afterwards, the lysates is packaged in pouches and finally stabilized by sterilization at 121° C., for 30 minutes.

The lysate obtained upon completion of the method as described according to Example 1 contains 4.5% by weight of dry matter, relative to the total weight of the lysate.

Example 2: Test In Vitro—Dose-Response Analysis of the TLRs (Invivogen)

HEK293-TLR Cell Lines:

The extract and the controls are tested in duplicate on recombinant HEK-293 cell lines. These cell lines functionally over-express human TLR proteins as well as a reporter gene that is a secreted alkaline phosphatase (SEAP). The production of this reporter gene is governed by an NFkB inducible promoter. The results of activation of the TLR reporters are given in the form of optical density (OD) values.

Positive Controls:

CU-T12-9 and FSL-1 are used on the cells expressing hTLR2 to respectively assess the TLR1/TLR2 and TLR2/TLR6 activities.

FSL-1 is tested at 10 μg/ml and 30 μg/ml. CU-T12-9 is tested at 200 nM and 300 nM.

Negative Controls:

A HEK-293 cell line recombinant only for the reporter gene has been used as a negative control for the cell lines expressing hTLR. To confirm the effectiveness of the inducible reporter gene NFkB (SEAP), this HEK-293 TLR cell line has been stimulated with TNFα at the following concentrations: 100 ng/ml, 30 ng/ml, 10 ng/ml, 3 ng/ml, 1 ng/ml, 0.3 ng/ml, et 0.1 ng/ml.

This negative control cell line has also been stimulated with the different concentrations of the tested extract.

Test of the Extract:

20 μl of the extract have been used to stimulate the reporter hTLR cell line in 200 μl of reaction volume. For the dose-response on the HEK-Blue-hTLR5 cell lines, the liquid extract obtained according to Example 1 has been tested in duplicate, at the following concentrations: 1000 μg/ml, 500 μg/ml, 250 μg/ml, 125 μg/ml, 62.5 μg/ml, 31.5 μg/ml. For the TLR1/2 and/or TLR2/6 specificity, the liquid extract obtained according to Example 1 has been tested in duplicate at the following concentrations: 100 μg/ml, 30 μg/ml and 10 μg/ml.

Results:

TABLE 2

Results on the cell line with hTLR2

| Tested compound - concentration | DO |
|---|---|
| CUT12-9 300 nM | 3.227 |
| Cut12-9 200 nM | 3.066 |
| FSL1 30 pg/ml | 2.174 |
| FSL1 10 pg/ml | 1.727 |
| Liquid extract obtained according to Example 1 100 μg/ml | 3.890 |
| Liquid extract obtained according to Example 1 30 μg/mL | 3.867 |
| Liquid extract obtained according to Example 1 10 μg/mL | 3.381 |

TABLE 3

| Results on the cell line with hTLR2-1 | |
|---|---|
| Tested compound - concentration | DO |
| CUT12-9 300 nM | 1.667 |
| Cut12-9 200 nM | 1.474 |
| FSL1 30 pg/ml | 0.013 |
| FSL1 10 pg/ml | 0.027 |
| Liquid extract obtained according to Example 1 100 μg/ml | 3.246 |
| Liquid extract obtained according to Example 1 30 μg/mL | 2.755 |
| Liquid extract obtained according to Example 1 10 μg/mL | 1.613 |

TABLE 4

| Results on the cell line with hTLR2-6 | |
|---|---|
| Tested compound - concentration | DO |
| CUT12-9 300 nM | 0.024 |
| Cut12-9 200 nM | 0.029 |
| FSL1 30 pg/ml | 2.047 |
| FSL1 10 pg/ml | 1.373 |
| Liquid extract obtained according to Example 1 100 μg/ml | 3.704 |
| Liquid extract obtained according to Example 1 30 μg/mL | 3.463 |
| Liquid extract obtained according to Example 1 10 μg/mL | 2.233 |

CONCLUSION

The extract does not activate the negative control cell line but strongly activates the reporter cell line hTLR2 (1/6) and that being so even at 10 μg/ml. It activates hTLR1/2 and hTLR2/6 in a non-specific manner.

Example 3: Test In Vitro—Modulation of the Expression of the Genes in Normal Human Keratinocytes

Materials and Methods

Cytotoxicity:

Normal human epidermal keratinocytes are sown in 96-well culture plates and then cultured at 37° C. and 5% of $CO_2$ in a culture medium for 24 hours. Afterwards, the medium has been replaced with a culture medium containing, or not (control), the compounds to be tested (8 tested concentrations), and the cells have been incubated afterwards for 24 hours. All conditions have been carried out in duplicate. At the end of the incubation, the cell viability has been measured by a standard test of measurement of the mitochondrial activity.

Analysis of the Expression of the Genes Associated to the Barrier Function/Hydration by RT-qPCT:

Normal human epidermal keratinocytes (NHEK) have been sown in 48-well culture plates and then cultured in a culture medium for 3 days at 37° C. and 5% of $CO_2$ with a renewal of the culture medium after first 24 hours of culture. At the end of the incubation, the culture medium has been replaced with a test medium (supplemented with 1.5 mM of $CaCl_2$)) containing no (control) or containing the compounds to be tested, and the cells has then been incubated for 24 hours. All conditions have been carried out in duplicate.

At the end of the treatments, the culture media have been eliminated and the cells have been rinsed twice with PBS (without $CaCl_2$, without $MgCl_2$). Afterwards, the total RNA has been isolated using an extraction kit. The quantification of RNA and its quality control have been analyzed by means of Labchip GX (Perkin Elmer).

The expression of the selected transcripts has been analyzed by quantitative PCR in two steps. First of all, the cDNAs have been transcribed in the opposite direction from the RNAs. Afterwards, the quantitative PCR experiments have been carried out using a real-time PCR system.

Experimental Protocol

The normal human epidermal keratinocytes are cultured and amplified to produce enough cells to assess up to 72 samples per campaign. 48-well microplates are sown with the cells (50,000 cells per well) and incubated for 48 hours in an environment at controlled temperature, humidity and $CO_2$. The samples to be tested are added on the cells upon a renewal of the culture medium and then the cells are incubated for 24 hours.

The cells are washed and dry frozen at −80° C. to preserve the RNA. The RNAs are extracted, quantified and their quality is checked before performing their reverse transcription into cDNA. Finally, an RT-qPCR is carried out for each experimental condition in order to quantify the expression of the set of selected genes.

TABLE 5

| Results | | | | |
|---|---|---|---|---|
| | | *Sphingomonas* Lyophilisate of the liquid extract obtained according to Example 1 | | Retinol |
| Average expression of the genes | | 0.2 g/L | 1 g/L | 1.00E−07 M |
| Gene group | gene | WATER | WATER | DMSO |
| Barrier function | Claudin 1 | 2.51 | 2.51 | 0.63 |
| | Cornifelin | 9.66 | 19.43 | 0.77 |
| | Zonula Occludens-1 | 3.81 | 3.87 | 1.61 |

In this example, a tested *Sphingomonas* batch corresponds to the lyophilisate (100% MS) of the liquid extract obtained according to Example 1 (4.5% MS).

In conclusion, taking into account the fact that 1 g/L corresponds to a concentration of 0.1%, the liquid extract obtained according to Example 1, allows for a significant modulation of the expression in NHEK at 0.0009 (calculation: 0.2×0.1×0.045) and at 0.0045% (calculation: 1×0.1×0.045) on the genes Claudin-1, Cornifelin and Zonula Occludens 1.

Example 4: Test In Vitro "Assessment of the Regulation of the PGE2 Release by Human Myeloid Cells"

Anti-inflammatory effectiveness test on the U937 human myeloid cell line (sourced from Dr. Kenneth NILSSON, a Cellular Pathology professor of the Immunology, Genetics, and Pathology department at Uppsala University, Rapphonsvagen 11, 75653 Uppsala, Sweden).

Principle of the Test

The cell line is used in this protocol to model the immune response of the monocytes/macrophages in vitro. The treatment with PMA and LPS induces the secretion of pro-inflammatory mediators and cytokines. The co-treatment with anti-inflammatory agents enables the identification of the intrinsic regulatory activity of the pro-inflammatory reaction in vitro.

Cellular Treatment

The human myeloid cell line has been treated with the *Sphingomonas xenophaga* extract in a RPMI 1640 culture medium supplemented with L-Glutamine, penicillin, streptomycin, fetal bovine serum heat-treated at 10%, 10 μg/mL of Phorbol 12-myristate 13-acetate (PMA) and 60 μg/mL of lipopolysaccharides for *E. Coli* (LPS). Seven concentrations of an extract of *Sphingomonas xenophaga* have been tested: 1, 3, 10, 30, 100, 300 and 1000 μg/mL.

Twenty-four hours after the treatment at 37° C. in a moistened atmosphere at 5% of $CO_2$, the cell viability has been measured for each condition.

Afterwards, the supernatants have been collected for the $PGE_2$ assay.

Cytokine Assay

The PGE2 levels are determined by the ELISA test.

Viability Calculation—CV75

$$CV75=C1+((V1-75)/(V1-V2))\times(C2-C1)$$

Where

C1=the lowest concentration with a viability >75%

C2=the highest concentration with a viability <75%

V1=the lowest viability percentage >75%

V2=the highest viability percentage <75%

Calculation of the Reactivity Index—RI

RI=amount of the marker (pg/ml) of the treated supernatants×100/amount of analytes (pg/ml) in the untreated supernatants.

Calculation of the Inhibiting Concentration at 50%—IC50

$$IC_{50}=C1+((50-RI1)/(RI2-RI1))\times(C2-C1)$$

Where

C1=the highest concentration with RI<50

C2=the lowest concentration with RI>50

RI1=the highest RI<50

R12=the lowest RI>50

TABLE 6

| Results | | |
|---|---|---|
| Dose of the extract in μg/ml | Viability in % | RI of $PGE_2$ expressed in % with respect to the control (solvent) |
| 1 | 101 | 102 |
| 3 | 102 | 88 |
| 10 | 101 | 92 |
| 30 | 103 | 91 |
| 100 | 103 | 72 |
| 300 | 101 | 28 |
| 1000 | 93 | 0.1 |

The *Sphingomonas* extract inhibits the section of the pro-inflammatory mediator with an IC50 equal to 199 μg/ml.

Example 5: Test In Vitro of the Effect of the Extract on the Secretion of the Cytokines (IL-6, IL-8, IL-10 and IL-12p40) by the Monocytes The objective of the experiment is to study the effects of the extract on the secretion of cytokines by the monocytes after 36 h.

Materials and Methods

Cellular Isolation and Culture:

The mononuclear cells have been obtained from leukocyte layers of healthy blood donors by a standard Ficoll-Hypaque gradient method. The monocytes have been isolated from the mononuclear cells by adherence to plastic for 2 hours in a serum-free medium (M-SFM) optimized for the culture of macrophages, at 37° C. in a moistened atmosphere containing 5% of $CO_2$. The adherent cells, highly enriched with monocytes have been incubated with tested compounds for 36 h.

Cytotoxicity Test:

During the last 6 hours, Alamar Blue is introduced in the cellular culture. Resorufin, a fluorescent molecule obtained by conversion of one of the components of Alamar blue, has been measured as an indicator of cell death. The measurement has been carried out thanks to the Tecan Infinite F500 spectrofluorometer.

Assay of the Cytokines:

After 36 h, the supernatants are collected and frozen at −80° C. until assay. The measurement has been carried out thanks to the milliplex assay kit (IL-6; IL-8; IL-10 et IL-12p40) on the Luminex LX100 apparatus.

Calculation Method for the Assessment of Results:

Since the ranges of values are different from one cytokine to another and in order to obtain a value that is easy to compare between the compounds, the multiplication factor is different depending on the cytokine compared to IL-10.

Comparison between IL-10 and IL-6: the ratio is IL-10×100/IL-6

Comparison between IL-10 and IL-12p40: the ratio is IL-10/IL-12p40

Comparison between IL-10 and IL-8: the ratio is IL-10×100 000/IL-8

The results are represented in FIG. 1. The product 2 corresponds to the liquid extract obtained according to Example 1.

The extract has immunoregulatory effects on monocytes: IL10>IL-6/IL-8/IL-12(p40). The extract induces a high production of IL-10 (anti-inflammatory cytokine) in terms of dose-response in comparison with IL-6 and IL-8 (pro-inflammatory cytokines).

Example 6: Test In Vitro of the Effect of the Extract on the Production of IgE by Human B Lymphocytes Stimulated with the Combination of Anti-CD40 and IL-4

In the study, the effect of the extract has been assessed on the IgE production by purified human B lymphocytes (isolation of the $CD19^+$ lymphocytes from mononuclear cells of the peripheral blood). More specifically, the IgE production has been induced by the stimulation of the B lymphocytes with the combination of anti-CD40 antibody and of IL-4. After 14 days of incubation, the amount of IgE released in the culture supernatants has been quantified using a specific ELISA kit. Concomitantly with the tested extract, 3 other molecules have also been assessed in this test. the reference standard CpG-ODN 2006 (a TLR9 ligand), as well as IFN-γ and PGE2 have been tested as reference compounds.

TABLE 7

| Studied compounds | | | |
|---|---|---|---|
| | Appearance/ Storage | Stock solution | Tested concentrations |
| **Tested compounds** | | | |
| Extract of Example 1 (lysate) | opaque liquid Storage: +4° C. away from humidity | The liquid at 4.6% in water is considered as a stock solution at 100% | 0.2% and 0.4% |
| **Reference compounds** | | | |
| CpG-ODN 2006 Invivogen, ref. tlrl-2006 | Powder Storage: −20° C. | 500 μM in ultrapure water | 3 μM |
| IFN-γ R&D Systems, ref. 285-IF-100/CF | Powder Storage: −80° C. | 200 μg/ml in ultrapure water | 10 ng/ml |
| $PGE_2$ Sigma, ref. P0409 | Powder Storage: −20° C. | 2.837 mM in ethanol | 1 μM |

Culture and Treatment

The B lymphocytes $CD19^+$ have been isolated, sown in 24-well plates and incubated over one night in the culture medium. Afterwards, the compounds to be tested, tested alone or in combination, and the reference compounds have been added, or not (controls), and the cells have been pre-incubated for 2 hours. Afterwards, the inducer (a CD40+ IL-4 combination) has been added, or not (unstimulated control) and the treatments with the test or the reference compounds have been repeated. Afterwards, the cells have been incubated for 14 days at a final density of $1.7\times10^6$ cells/ml).

All experimental conditions have been carried out in n=3.

Enzyme-Linked Immunosorbent Assay (ELISA)

The amount of IgE released in the culture supernatants has been measured using a specific ELISA kit according to the instructions of the supplier.

Statistics

The inter-group comparisons have been performed through an unpaired Student's t-test. The statistical analysis can be interpreted if n 5, however for n<5 the statistical values are given for indication.

Formulas Used in this Report:

Mean Standard Error:

$$MSE=Sd/\sqrt{n}$$

The mean standard error (MSE) is a measurement of the deviation between the average of the sample and the actual average of the population. The MSE is calculated as the standard deviation of the sample (Sd) divided by the square root of the size of the sample (n).

Results and Conclusion

In unstimulated conditions, the baseline of release of IgE by the B lymphocytes is very low (<199 pg/ml, close to the detection limit). Stimulation for 14 days by the antiCD40+ IL-4 combination, has led to a high level of IgE production (3657 pg/ml). The TLR9 CpG-ODN2006 agonist, tested as a reference compound at 3 μM, has completely inhibited the IgE production induced by the antiCD40+IL-4 association (<3% of the stimulated control). These results were expected and have validated the test.

The other two potential reference compounds have also shown an inhibiting effect on the IgE production but to a lesser extent in comparison with CpG-ODN2006. The IFN-γ, tested at 10 ng/ml, has also shown a quite strong and significant inhibiting effect (20% of the stimulated control). However, the effect of $PGE_2$ tested at 1 μM was much more limited and statistically not significant (58% of the stimulated control).

The extract of Example 1, tested at 0.2% and 0.4%, has shown an almost complete inhibiting effect on the production of IgE by the B lymphocytes stimulated by the combination antiCD40+IL-4 (<3% and <11% of the stimulated control, respectively).

In the experimental conditions of this study, the different concentrations of the extract of Example 1 have shown a very powerful inhibiting effect on the IgE production by the cells B stimulated by the anti-CD40+IL-4 combination.

TABLE 8

| Summary of the results | | | | | | | |
|---|---|---|---|---|---|---|---|
| | Tested compound and concentration | IgE | Mean (pg/ml) | SEM (pg/ml) | % of the stimulated control | SEM % | p |
| Unstimulated control | — | 349<br><123<br><123 | <199 | 75 | <5 | 2 | ** |
| Anti CD-40 10 μg/ml + IL-4 | Control | 3076<br>4924<br>2970 | 3657 | 634 | 100 | 17 | * |
| 10 ng/ml | CpG-ODN 2006 3 μM | <123<br><123<br><123 | <123 | 0 | <3 | 0 | ** |
| | IFN-γ 10 ng/ml | 1012<br>166<br>1036 | 738 | 286 | 20 | 8 | * |
| | $PGE_2$ 1 μM | 2942<br>1495<br>1941 | 2126 | 428 | 58 | 12 | ns |
| | *Sphingomonas* extract of Example 1 (lysate) 0.2% | <123<br><123<br><123 | <123 | 0 | <3 | 0 | ** |

TABLE 8-continued

| Summary of the results | | | | | | |
|---|---|---|---|---|---|---|
| Tested compound and concentration | IgE | Mean (pg/ml) | SEM (pg/ml) | % of the stimulated control | SEM % | p |
| *Sphingomonas* extract of Example 1 (lysate) 0.4% | <123<br><123<br>958 | <402 | 278 | <11 | 8 | ** |

ns: >0.05 not significant
* 0.01 to 0.05 significant
** 0.001 to 0.01 very significant
< or >: below or above the detection limit
<123.457 or >90,000 pg/ml for undiluted samples In the case of a value below or above the detection limits, the following calculations are extrapolated.

Example 7

A gel having the following composition has been prepared:

TABLE 9

| Composition of the gel | |
|---|---|
| Compound | Amount (in g) |
| Lyophilisate of the liquid extract obtained according to Example 1 | 1 g |
| Xanthan gum | 0.5 g |
| Preservatives | qs |
| Water | qs 100 g |

The obtained composition has been applied on a face with an allergy-prone skin.

The invention claimed is:

1. A method for preventing or treating cutaneous reactions caused by an allergic reaction comprising the administration of an extract from non-genetically modified bacteria of the species *Sphingomonas xeophaga*, wherein the extract:
   - has an activity in activating the hTLR2 receptors and/or in promoting the expressions of genes related to the reinforcement of the barrier function of the skin; or
   - has an activity in inhibiting the secretion of the pro-inflammatory mediator $PGE_2$; or
   - has an activity in stimulating the expression of IL-10 without significantly impacting the expression of IL-12, IL-6 and IL-8; or
   - has an activity in inhibiting the production of IgE by B lymphocytes.

2. A method for preventing or treating cutaneous reactions caused by an allergic reaction comprising the administration of a composition comprising:
   - a.—an extract from non-genetically modified bacteria of the species *Sphingomonas xeophaga*, or
   - b.—at least one non-genetically modified bacterium of the species *Sphingomonas xeophaga;* wherein the extract:
   - has an activity in activating the hTLR2 receptors and/or in promoting the expressions of genes related to the reinforcement of the barrier function of the skin; or
   - has an activity in inhibiting the secretion of the pro-inflammatory mediator $PGE_2$; or
   - has an activity in stimulating the expression of IL-10 without significantly impacting the expression of IL-12, IL-6 and IL-8; or
   - has an activity in inhibiting the production of IgE by B lymphocytes.

3. The method according to claim 1, wherein the extract is obtained from the non-genetically modified bacteria of the strain filed under the CNCM accession number I-5455.

4. The method according to claim 1, wherein the administration is a topical administration.

5. The method according to claim 2, wherein the concentration of the extract is between 0.0001% and 30% by weight with respect to the total weight of the composition.

6. The method according to claim 2, wherein the composition further comprises at least one active substance selected from the group consisting of acetyl dipeptide-1 cetyl ester, an extract of *Salvia miltiorrhiza* root, a thermal water and mixtures thereof.

7. The method according to claim 1, wherein the allergic reaction is an immediate-type allergic reaction.

8. The method according to claim 1, wherein the reaction comprises urticaria, a cutaneous eruption and/or the apparition of redness.

9. A method for modulating the immune response, comprising the administration of an extract from non-genetically modified bacteria of the species *Sphingomonas xeophaga*, wherein the extract:
   - has an activity in activating the hTLR2 receptors and/or in promoting the expressions of genes related to the reinforcement of the barrier function of the skin; or
   - has an activity in inhibiting the secretion of the pro-inflammatory mediator $PGE_2$; or
   - has an activity in stimulating the expression of IL-10 without significantly impacting the expression of IL-12, IL-6 and IL-8; or
   - has an activity in inhibiting the production of IgE by B lymphocytes.

10. A method for modulating the immune response, comprising the administration of a composition comprising:
   - a.—an extract from non-genetically modified bacteria of the species *Sphingomonas xeophaga*, or
   - b.—at least one non-genetically modified bacterium of the species *Sphingomonas xeophaga;* wherein the extract:
   - has an activity in activating the hTLR2 receptors and/or in promoting the expressions of genes related to the reinforcement of the barrier function of the skin; or
   - has an activity in inhibiting the secretion of the pro-inflammatory mediator $PGE_2$; or has an activity in stimulating the expression of IL-10 without significantly impacting the expression of IL-12, IL-6 and IL-8; or has an activity in inhibiting the production of IgE by B lymphocytes.

11. The method according to claim 2, wherein the non-genetically modified bacteria are of the strain filed under the CNCM accession number I-5455.

12. The method according to claim 2, wherein the administration is topical administration.

13. The method according to claim 2, wherein the allergic reaction is an immediate-type allergic reaction.

14. The method according to claim 2, wherein the reaction comprises urticaria, a cutaneous eruption and/or the apparition of redness.

15. The method according to claim 3, wherein the administration is topical administration.

16. The method according to claim 4, wherein the concentration of the extract is between 0.0001% and 30% by weight with respect to the total weight of the composition.

17. The method according to claim 10, wherein the concentration of the extract is between 0.0001% and 30% by weight with respect to the total weight of the composition.

* * * * *